United States Patent [19]

Shair

[11] 3,991,626
[45] Nov. 16, 1976

[54] ANALYSIS SYSTEM FOR AN ATMOSPHERE TRACER DISPERSION SYSTEM

[75] Inventor: Frederick H. Shair, Altadena, Calif.

[73] Assignee: California Institute of Technology, Pasadena, Calif.

[22] Filed: Apr. 7, 1975

[21] Appl. No.: 565,780

[52] U.S. Cl. .......................................... 73/421.5 R
[51] Int. Cl.² ........................................... G01N 1/24
[58] Field of Search ............... 73/421.5 R, 422 GC, 73/425.6, 23.1; 128/234–237

[56] References Cited
UNITED STATES PATENTS

| | | | |
|---|---|---|---|
| 2,724,385 | 11/1955 | Lockhart | 128/234 X |
| 3,338,087 | 8/1967 | Moberg et al. | 73/421.5 R X |
| 3,886,800 | 6/1975 | Boehringer | 73/425.6 |

*Primary Examiner*—James J. Gill
*Attorney, Agent, or Firm*—Marvin E. Jacobs

[57] ABSTRACT

A system for atmospheric monitoring is disclosed. Atmospheric dispersion of a plume is monitored by continuously releasing a tracer gas such as sulfur hexafluoride into the plume, collecting air samples downwind and analyzing the samples. The system includes plastic piston pump samplers having a locking outlet receiving removable nozzles or a lock-seal closure. The samples are analyzed by means of a tracer specific gas-chromatograph-electron capture (GC-EC) detector having a lock-seal inlet adapted to engage the sampler outlet. In a preferred system, the atmospheric samples are collected by automatic, sequentially operated samplers and analyzed by means of a plurality of GC-EC detectors operating in parallel such that the trailing oxygen band is eluted through the first detector as the last detector is being loaded. Thus, the system is in continuous operation and minimizes operator time, and 80 samples can be analyzed in one hour. A multiple input, digital integrator having means for integrating peaks formed during baseline drift provides continuous, reliable read-out data from the signals from the multiple GC-EC detectors.

3 Claims, 7 Drawing Figures

TIME FROM INJECTION, MIN

ANALYSIS SYSTEM FOR AN ATMOSPHERE TRACER DISPERSION SYSTEM

BACKGROUND OF THE INVENTION

1. Field of the Invention

The present invention relates to atmospheric dispersion monitoring and, more particularly, to a system for tracing atmospheric dispersion by means of release, collection and analysis of one or more tracer gases, particularly sulfur hexafluoride.

2. Description of the Prior Art

The spread and dilution of atmospheric contaminants from real sources over distances and in time is of great practical concern. Both small and large scale information is necessary for design of ventilation systems in buildings, location of residential communities with respect to dispersion of pollutants from an urban highway, pollutant flow within the wake downwind of a building and the large scale transport and dispersion within a single basin and extending into adjacent basins.

In general, models for predicting atmospheric dispersion of pollutants over long distances can be divided into two classes: those which assume that concentrations vary in a Gaussian manner, commonly known as Gaussian plume models, and those which use the concept of an eddy diffusivity, commonly known as K-theory. However, in many cases the air flow is so complicated that theoretical solutions of the governing fluid mechanics equations prove intractable. Experimental tracer studies become a necessity in these cases providing basic concentration data for the formulation of equations describing the dispersion process. Before any theory of atmosphere dispersion can be considered valid, it must be compared with experimental observations of a tracer substance which moves and disperses within the main air flow.

Many different types of tracers have been used to experimentally study atmospheric dispersion. Three general categories of tracers have been considered: optical outline methods, trajectories of individual markers, and chemical tracer substances which disperse along the flow. Oil-fog, dense black smoke has been commonly used in optical outline tracer tests. The problem with optical outline methods is that they are generally limited to close distances from the source and dilution factors can be only roughly estimated from photographs.

The trajectories of balloons equipped with radar transponders can be individually followed for fairly long distances. However, balloons can only be used for wind speed and direction data; information on the dilution of pollutant concentrations is not possible.

For accurate dilution information, chemical tracer substances which disperse along the main flow must be used. Chemical tracers can be categorized as particulates and gases. The most widely used tracer substance has been a fluorescent particulate mixture of zinc and cadmium sulfide, sometimes referred to as simply FP tracer. After release of the tracer, the analysis required drawing an air sample through filter paper and then counting the number of fluorescent particles trapped on the paper under ultraviolet light. This tracer technique, though widely used, will decline in the future because the tracer has been classified as toxic which limits its use in heavily populated areas and another problem is that at distances of 60–70 km, typically 50–80% of the particles had settled out and been lost.

Gaseous tracers have a distinct advantage over particulate tracers since they do not settle out due to gravitational forces. Several radioactive gaseous tracers have been utilized and have been traced for distances as great as 160 miles. With caution, these tracers may be suitable for testing small-scale ventilation problems, but are not appropriate for use over populated areas. Even when used in dilute amounts for testing the ventilation in the room, the experimenter must monitor concentrations remotely from another room.

Sulfur dioxide has been used to monitor dispersion downwind of a power plant. However, sensitivity measurement is a problem as is interference from existing and interfering background $SO_2$ concentrations. A recent study suggested measuring sulfur-32 to sulfur-34 isotope ratios with a mass spectrometer as a method for tracing stack emissions. In small enclosures, initial high levels of the order of 0.5% of various tracer gases such as helium, nitrous oxide or volatile organic solvents can be introduced to overcome sensitivity problems in the analysis.

Recent advances in analytical chemistry have made possible extremely sensitive measurements of certain gaseous compounds. The principle of detection is based on the fact that these gases have a very high affinity for capturing electrons, and if these gases are introduced into a small electric current, the measured current will increase. The electron capture detector is a substance specific device. It is extremely sensitive to certain molecular species which react with free electrons to form stable negative ions such as molecules containing electron absorbing groups such as halogens, carbonyl, nitro or certain condensed ring aromatics. However, the EC detector has very low sensitivity for hydrocarbons other than fused ring aromatics and importantly it can reliably detect halogenated hydrocarbons in quantities as low as $10^{-10}$ to $10^{-12}$ and, under optimized conditions, $10^{-14}$ concentrations have been detected.

Studies of the sensitivity of electron capture detectors for a large number of halogenated compounds showed that sulfur hexafluoride, an inert non-toxic gas, had one of the highest responses, and can be detected in quantities of as low as $10^{-13}$ parts $SF_6$ per part of air. $SF_6$ is chemically inert at normal temperatures, is stable to ultraviolet light and is extremely insoluble in water. When animals were exposed to atmospheres consisting of 80% $SF_6$ and 20% $O_2$ for periods of 16–24 hours, no indications of intoxication, irritation or any other symptoms were observed during the exposures or any time thereafter. Human subjects were recently exposed to a breathing mixture of 90% $SF_6$ and 10% $O_2$ under pressure of 2 atmospheres. In a similar study, dogs were exposed to a breathing mixture of 95% $SF_6$ and 5% $O_2$ at a pressure of 4 atmospheres. No mention of any abnormal or toxic effects was made in either of the latter two studies.

Thus, since it is gaseous, physiologically inert, chemically inert, and easily detectable in extremely low concentrations, sulfur hexafluoride is an excellent atmospheric tracer. Long range studies have shown that $SF_6$ can be detected with ease beyond 70 miles away from a continuous point source. The extreme sensitivity of this tracer which can readily be measured at one part in $10^{12}$ is necessary for large-scale tracer tests. As an example of the sensitivity, if only 100 lbs of $SF_6$ were allowed to evenly disperse up to a height of ¼ mile, the tracer could be detected over an area of 8,000 square miles, which is approximately the area of the state of Massachusetts.

Tracer studies require the collection of air samples to be returned to the laboratory for analysis or for analysis at the field site using portable equipment. To obtain ambient air samples, sometimes called grab samples, previous studies have utilized evacuated stainless steel cylinders, glass containers, plastic bags and plastic squeeze bottles. Steel cylinders are extremely effective for samples since there is low absorption, and the time for sampling can be easily adjusted. However, stainless steel cylinders are expensive and quite bulky. Glass containers are not suitable since the surface charge on the glass surface adsorbs electron absorbing compounds such as $SF_6$. Plastic bags are relatively inexpensive; however, they are also bulky and require a pump which can contaminate an air sample. Plastic squeeze bottles are inexpensive, take up little space and can be easily cleaned for reuse. The sampling procedure requires squeezing the bottle hard 10 successive times, one squeeze a second. Though this procedure shows good reproducibility, it requires the presence of an operator to open, collect and close the sample bottle and the bottle is not readily adaptable for automated sampling or analysis.

The gas chromatograph-electron capture analysis devices that are commercially available are not specifically designed for tracer gas analysis, are unnecessarily complex, bulky, and expensive and must be modified in order to be suitable for use in such studies.

SUMMARY OF THE INVENTION

The present invention relates to a system for large-scale atmospheric field studies. The component parts of the system are relatively inexpensive, capable of simple, effective and accurate operation such that the study can be conducted and the results analyzed within a 24-hour period by technician level personnel. The total system can be operated by a single personnel who injects the tracer, collects the samples and analyzes them at the field site or returns them to the laboratory for continuous analysis by means of the multiple parallel analyzer feature of the apparatus of the invention. The training period for personnel is very short, the cost of tracer gas is low making this system very attractive from economical and operational considerations. Man hour requirements for large-scale studies can be further reduced by utilization of remote controlled start sampling devices or by use of a timer for delayed starting of a remotely located air sampler.

Other aspects of the invention relate to the use of plastic syringes as the piston pump sampler having an outlet lock-assembly for engaging the nozzle and to the use of closures and GC-inlet assemblies, adapted to engage the lock-assembly. The syringes, typically of the 10 to 50 cc capacity, are small, light, compact and non-breakable facilitating ready transport of large numbers for large-scale field studies. They are easy to evacuate and can be reliably filled over short or long sampling periods. They are readily adapted to automated filling for remote sampling in accordance with other features of the invention.

The system of the invention comprises a combination of a volatile specific tracer, a plastic piston pump sampler having lock-seal closure outlet means and a tracer specific gas chromatograph-electron capture (GC-EC) detector having a lock-seal inlet adapted to engage the sampler outlet. In a more preferred embodiment, the system operates with $SF_6$ or related compounds as the tracer, and utilizes a plurality of automatic, sequentially operated samplers. The samples are analyzed by means of a plurality of GC-EC detectors operating in parallel such that the first detector is eluting the trailing oxygen band as the last detector is being loaded. Thus, the system is in continuous operation and minimizes operator time to analyze the samples from a large-scale air pollutant transport study.

These and many other attendant advantages of the system will become apparent as the invention becomes better understood by reference to the following detailed description when considered in conjunction with the accompanying drawings.

DESCRIPTION OF THE PREFERRED EMBODIMENTS

Figure 1:
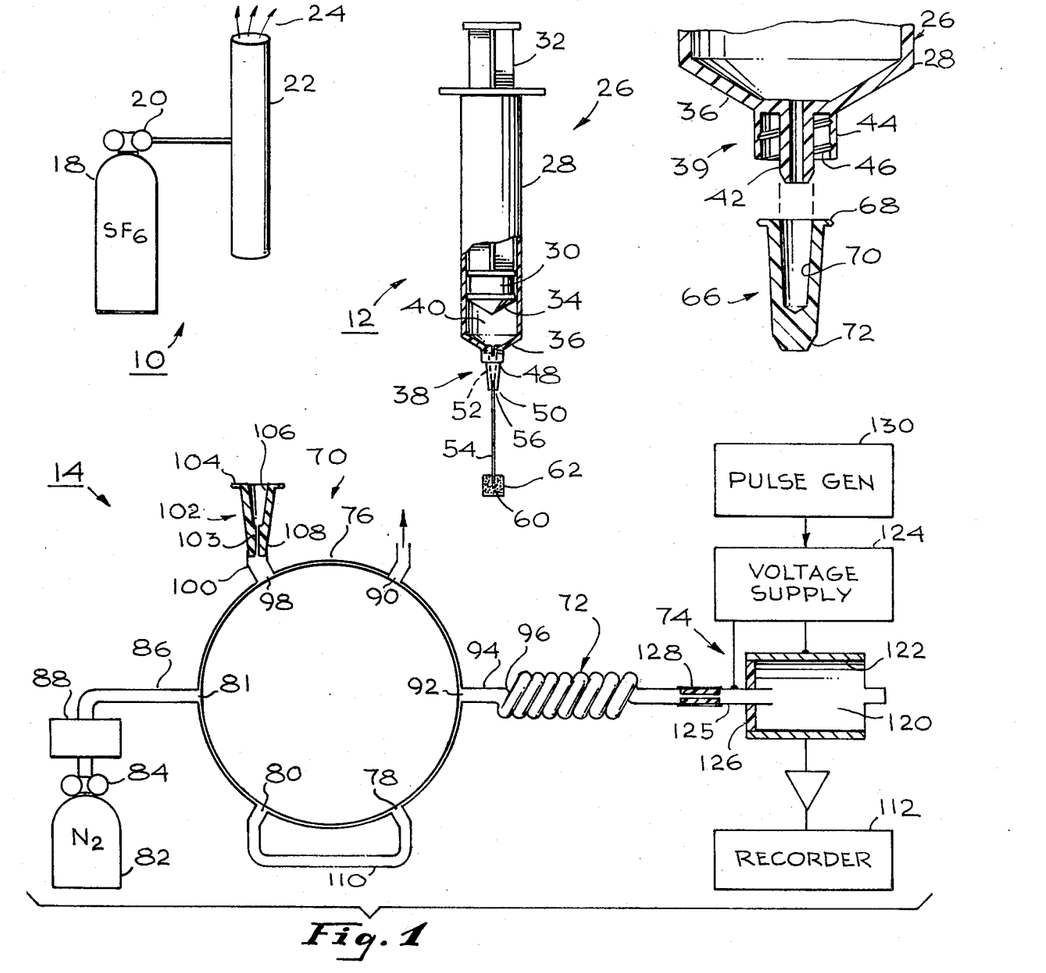
FIG. 1 is a schematic and plan view, partly in section of the plume tracer analysis system of the invention.

Referring now to FIG. 1, the pollution detection system of the invention generally includes tracer release section 10, air sample collection station 12 and analysis section 14. The release site may be a point source such as a stack or a continuous line source such as an automobile moving along the highway. The tracer is continuously released in a predetermined, controlled rate from a supply such as a cylinder 18 through a metering valve 20 into the stack 22. The rate of release depends on the inversion layer, wind velocity and the distance downwind that the plume is to be followed. The cost of the tracer is also a consideration. However, a rate of supply of tracer release such that it reaches a concentration of 1–2 ppm at the exit 24 to the stack under normal wind conditions will allow detection at $10^9$ to $10^{12}$ parts 30 miles downwind.

Wind direction may be determined by weather vanes or by releasing balloons into the atmosphere surrounding the stack 22. The samplers downwind from the stack 22 at the collection station 12 are installed in an evacuated condition. The sampler is a piston pump syringe 26 comprising a cylindrical housing 28 in which is mounted an elastomeric piston 30 connected to an elongated plunger member 32. The piston member 30 has a lower conical face 34 which abuts the lower end 36 of the housing 28 on full insertion of the plunger 32. On withdrawal of the plunger 32, air is drawn in through the nozzle assembly 38 into the evacuated chamber 40 of the syringe.

The housing 28 terminates in a nozzle assembly 38 which includes a lock assembly 39 adapted for removal and replacement in a sealing manner of the needle-like nozzle 50. A cylindrical outlet tube 42 suitably formed of resilient deformable plastic is positioned at the apex of the bottom wall 36 of the housing 28. Spaced outwardly from and concentrically from the tube 42 is a shorter, cylindrical locking member 44 having internal threads 46. The outer shoulder 48 of the nozzle member 50 engages the threads 46 while the tapered interior portion 52 thereof sealingly engages the tip of the nozzle outlet 42 as the shoulder 48 engages the threads 46. The conical member 52 is suitably formed of a deformable plastic. The elongated needle nozzle 53 usually formed of stainless steel is sealingly received into the member 52 typically by heat sealing at the tip 56 or by means of a potting compound.

After withdrawal of the plunger 32 and collection of tracer tagged air sample within the chamber 40, the tip 60 of the needle nozzle 54 may be temporarily sealed by applying to he tip a plug of soft, resilient material 62. If the analysis is to be conducted immediately in the field, the operator may proceed to inject the sample into the detection section 14. Usually, however, with largescale field studies, the sampler must be capped during transport and handling before analysis. In accordance with the invention, the nozzle assembly 38 is removed and a sealing-locking cap member 66 is applied to the syringe 26. The plug member 66 is of similar configuration to the nozzle assembly 38 in that it includes a shoulder member 68 engaging the threads 46 and an internal conical recess 70 adapted to sealingly engage the plastic member outlet 42 on threading of shoulder 68 into threads 46. The terminal portion 72 of the plug member in this case is sealed.

The syringe, in withdrawn condition containing the tracer tagged air sample and closed with plug member 66, is now ready for analysis. The analysis section 14 of the invention includes a sampling section 70, a gas chromatographic column 72 and an electron capture detector 74. The sampling section 70 includes a six-port valve 76. Ports 78 and 80 are connected to a sample loop of known volume. Port 81 is connected to a regulated nitrogen carrier gas supply cylinder 82 on which is mounted regulator valve assembly 84. The carrier gas is fed through line 86 containing a molecular sieve filter 88 to remove any traces of water from the carrier gas supply. Port 90 is connected is vent while port 92 is connected to line 94 which leads to the inlet 96 to the GC column 72.

Port 98 is connected to the sample inlet 100 on which is mounted an inlet assembly 102 adapted to receive the syringe in a sealing-locking member. The inlet assembly 102 is similar to the plug assembly 66 and includes an outer shoulder member 104 adapted to engage the threads 46 of the syringe 26 and an inner conical recess 106 which sealingly engages the member 42 when the shoulder 104 is screwed into the threads 46. The member 102 has an aperture 103 at the bottom apex of the conical section 108 through which the tracer tagged sample enters the inlet pipe 100.

During sample injection, the six-port valve is positioned such that port 98 is connected to port 78 and port 80 is connected to the vent port 90. After a calibrated volume of sample is contained within the sample loop 110, port 80 is connected to port 92 while port 81 is connected to port 78 and valve 84 is opened. A regulated flow of purified nitrogen carrier gas sweeps through the sample loop 110 and a measured amount of tracer tagged air sample is delivered to the column 72 through tube 94. A characteristic peak indicative of the amount of the tag is determined in the EC detector 74 which may be recorded on recorder 112.

Correlation between chemical structure and column retention times is well recognized. Gas chromatography provides distinct, separation between the components of the air sample and is only sensitive with respect to those compounds of the air sample having the high electron affinity such as the gaseous tracer and oxygen. In the case of $SF_6$, the $SF_6$ band is eluted first followed by oxygen. The column 74 is suitably an elongated cylinder of stainless steel which may be bent into a coiled form and contains a chromatographic retardant suitably an aluminum silicate such as molecular sieve 5A. The column is typically from about 4 to 10 feet in length, ¼ to ⅛ in. in diameter.

The chamber 120 of the EC detector 74 is an ionization chamber which may be of many configurations such as plain, parallel or axial. A preferred configuration is an axial chamber, the interior wall of which is lined with a sheet of metal such as titanium coated with a thin layer of a tritium source which forms the cathode 122. A polarizing voltage supply 124 applies a potential across the detector 74. Free electrons are created in the chamber 120 by means of the radiation source 122. The anode 125 is in the form of a coaxial tube mounted in an insulating disc 126 at the front end of the detector 74. The anode 125 is electrically isolated from the outlet of the gas chromatograph column 72 by means of an insulating spacer element 128 suitably formed of a resilient plastic such as nylon or Teflon having low relase of volatile compounds that could interfere with the analysis. The density of free electrons in the chamber 120 is measured by periodically applying to the anode 125 a rectangular sampling pulse from a pulse generator 130. The duration of the pulse is chosen to be just sufficient to collect all the electrons set free in the chamber, that is, capable of withdrawing a saturation current from the chamber. Such a pulse duration is too short to collect any of the relatively slow moving negative molecular ions.

The principle of detection is based on the fact that gaseous halogenated compounds have a very high affinity for capturing electrons and if these gases are introduced into a small electric current, the measured current will decrease.

Compounds which strongly capture electrons have one or more of the following electrophore structures or substituents in their molecules:

1. —CO.CO—
2. —CO.
3. Quinone
4. —$NO_2$
5. —X, where X is halogen.

With substitution, the halogen affinities fall in the order I>Br>Cl>F. Multiple substitution by halogen more than linearly enhances the affinity for electrons. The gaseous Freons, chlorofluoro-substituted hydrocarbons such as Freon 11 are suitable tracers depending on the background concentration in the vicinity of the test. $SF_6$ and its telomers are not typically present in the atmosphere and are preferred tracers in the system of this invention. The homologous telomers of the formula:

$$SF_5(CF_2)_nZ$$

where $n$ is an integer from 0–25 and Z is F, Cl, Br or I give very high responses.

The use of a radioactive source as the cathode provided a low electron density and greatly increases sensitivity. A pulsed applied voltage allows more efficient capture of electrons.

There are two electron emitting radiaoactive sources which are commonly used in electron caption detectors, tritium and nickel-63. Tritium, which is fairly inexpensive, is normally chemically bonded to a titanium substrate and is useful at operating temperatures under 200° C. Very small quantities of oxygen or water vapor in the carrier gas can have a large effect on the electron capture detector. However, by the use of the molecular sieve trap 88 to remove water vapor from the carrier gas, the standing current is independent of temperature and there is no necessity to provide temperature control on the detector chamber 120. Optimum pulsing of the electron capture detector can lead to a detection limit better than $10^{-13}$ parts $SF_6$ per part of air. With the preferred concentric electrode chamber, optimum pulsing occurs with a 30–40 volt pulse having a pulse width of 1 microsecond at a pulsing period of from about 150 to 200 microseconds, preferably about 180 microseconds. Another preferred aspect of the invention relates to the use of a crystal-controlled oscillator utilizing digital integrated circuits for the pulse generator. Thus, the GC-EC is capable of battery operation and can be utilized in a portable mode for mounting in a car or van for on-field analysis of the samples.

Figure 2:
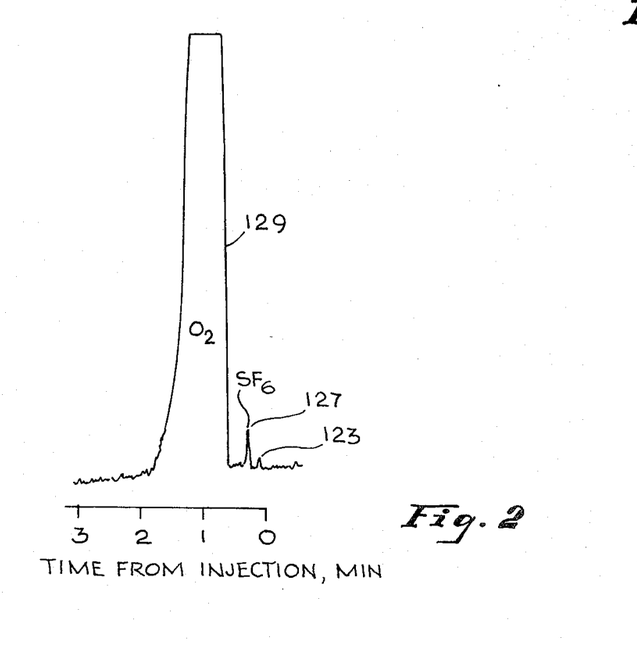
FIG. 2 is a calibration curve consisting of a set of strip chart recorder peaks showing the EC detector response to a collected sample.

Under these conditions with a flow rate of 90 ml per minute and an 8 foot ⅛ inch stainless steel column packed with 80–100 mesh 5A molecular sieve, the $SF_6$ peak is eluted first as a sharp peak in about 20 seconds after injection, followed by a large oxygen peak which appeared about 45 seconds after injection and was completely eluted in about 3 to 4 minutes. A typical separation of a low $SF_6$ concentration ($5 \times 10^{-12}$ parts $SF_6$ per part of air) and oxygen is shown in FIG. 2, as provided by the electrometer output monitored by a strip chart recorder. After a short pressure pulse 123, the sharp $SF_6$ peak 127 appears followed by the longer oxygen peak 129. An RC filter with a time constant of 0.3 to 0.5 seconds can be utilized to reduce high frequency noise.

Figure 3:
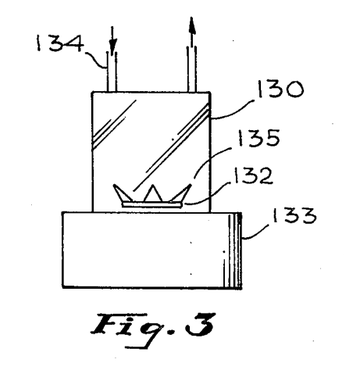
FIG. 3 is a front elevational view of the calibration gas source.
Figure 4:
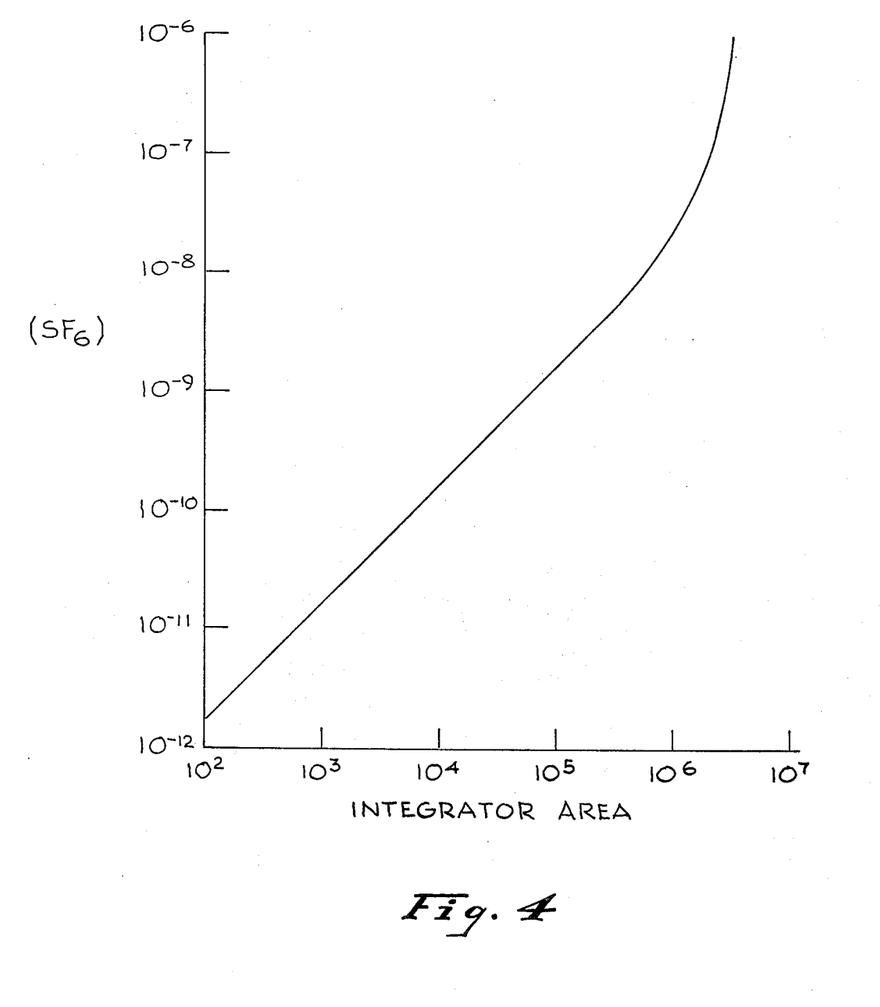
FIG. 4 is a calibration curve for $SF_6$, with integrator area as the abscissa and $SF_6$ concentration as ordinate.

Calibration of the chromatograph can be accomplished by a well-mixed exponential dilution system. As shown in FIG. 3, a 6 × 6 × 6 inch lucite cube 130 contains a magnetically driven propeller 132 on which are mounted vanes 135. The cube is mounted on a magnetic stirring unit 133. An initial concentration of approximately 1 ppm of sulfur hexafluoride is introduced into the cube 130. A slow flow rate of high purity compressed air is then added through inlet 134 which results in one complete air exchange in about 30 minutes. If the gases within the cube 130 were well mixed, the dilution would follow the equation:

$$c = c_0 e^{-\frac{qt}{v}}$$

where $c_0$ is the initial concentration, $q$ is the flow rate of air through the air chamber, $t$ is time elapsed from injection of tracer and $v$ is volume of the chamber. A graph of log peak area versus the number of air changes should yield a slope of $-1$ as shown in FIG. 4. A typical calibration curve of integrated peak area versus $SF_6$ concentration is shown in FIG. 4. The minimum detectable $SF_6$ concentration defined as 3 times the peak to peak noise level was about $1.0 \times 10^{-12}$ or better for the GC-EC system. The GC-EC system has a linear dynamic range of approximately $10^3$ from $SF_6$ concentration of $10^{-12}$ to $10^{-9}$. At higher concentrations the 200 millicuries concentric electrode system electron capture detector becomes nonlinear with respect to the tracer concentration. However, with electronic digital integration, calibration is possible up to 1 ppm $SF_6$ by reference to a calibration chart.

Figure 5:
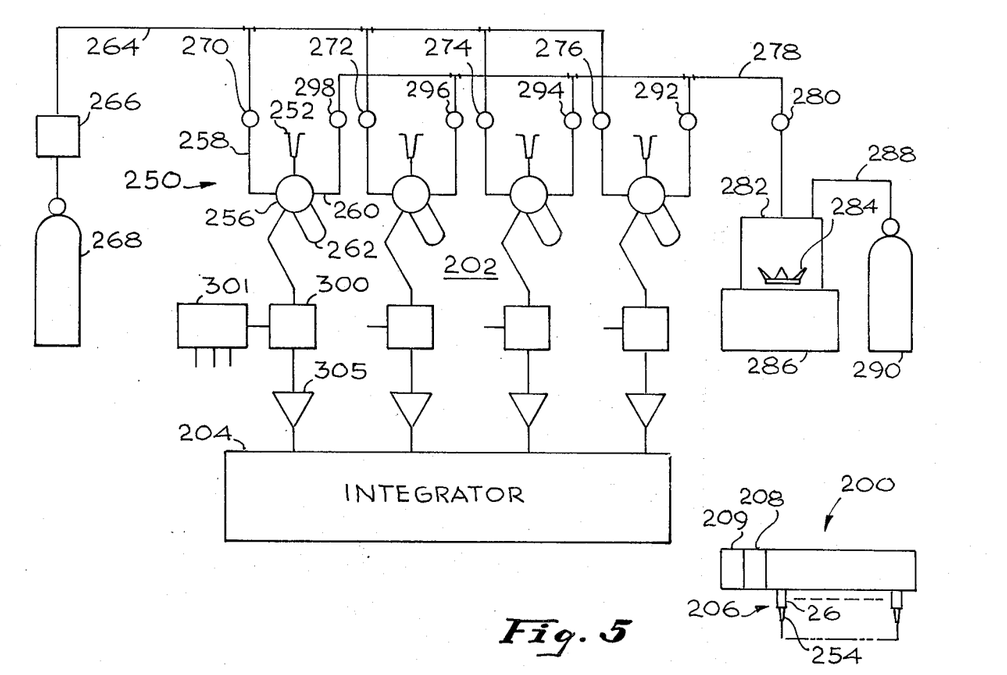
FIG. 5 is a schematic view of a multiple-mode analytical atmospheric tracer system.

A highly efficient, multiple-mode system is illustrated in FIG. 5. The system includes a remote sequential air sampling unit 200 including a plurality of the air-sampling syringes 206 described in FIG. 1 and an analysis section including a plurality of GC-EC analyzers 202 connected to a multiple input digital integrator 204.

The sampling unit 200 contains a plurality of spring-loaded syringes 206, suitably 4–12, which are released sequentially by the motion of a rotary mechanical timer 208. Field tests have established that the sampling unit 200 can take accurate sequential samples automatically and contain each sample without leakage for at least a period of 18 hours in an outdoors environment. The samples can be taken instantaneously (10 seconds) or averaged over a one-hour period with less than 1% diffusion. The timer 208 may include provision for delayed start of the sampling sequence until the plume being monitored reaches the location of the sampler or the sampler timer 208 may be activated remotely by means of a signal actuated servo 209. The sampling unit is described in copending application Ser. No. 482,140, filed June 24, 1974, the disclosure of which is incorporated herein by reference.

Figure 6:
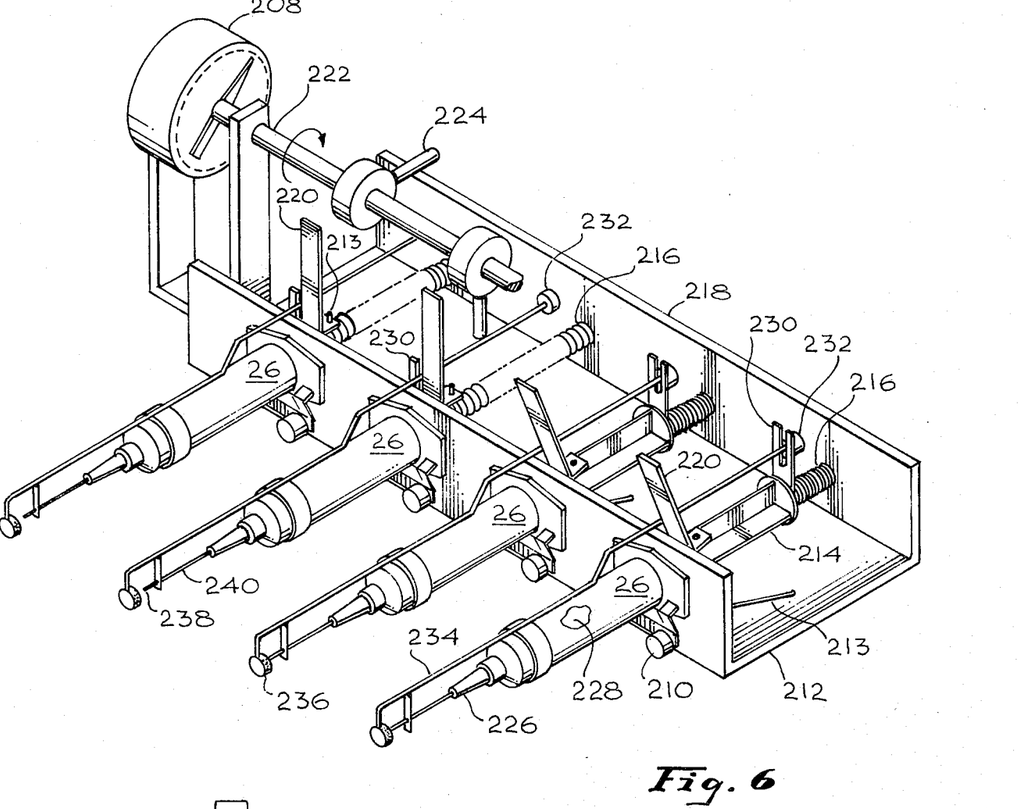
FIG. 6 is a perspective view of an automated sequential atmospheric sampler.

Referring now to FIG. 6 four 20–50 cc plastic syringes 26 are attached by a thumb screw mechanism 210 to the outside of a length of metal channel 212. The plunger 214 of each syringe is attached to a strong spring 216 which is anchored at the rear 218 of the channel 212.

To spring load each syringe, the spring is extended across the entire width of the channel and latched at the forward edge by a metal pin 213 held in place by an L-shaped lever arm 220 as illustrated with respect to the rear two fully spring-loaded syringes. The rotary mechanical timer 208 is connected to a shaft 222 containing an adjustable metal arm 224 positioned at spaced radial and lengthwise positions along the shaft. As the timer 208 turns the shaft 222, the radial arms 224 sequentially engage and push each L-shaped lever arm 220 forward to release the metal pin 212 which latches the spring 216. The released spring pulls the plunger 214 rearwardly and draws in an air sample through nozzle 226 into the collection chamber 228.

Near the end of the withdrawal of the plunger 214, the plunger engages a U-shaped guide plate 230 which engages the stop disc 232 and pulls the guide rod 234 which forces an elastomeric closure 236 against the tip 238 of the needle nozzle 240 as shown with respect to the forward two syringes.

The timer 208 can be mechanical or electrical and the sampling period and rate of collection are readily adjustable individually for any of the samplers. The timer can be set for delayed starting or a remote controlled actuator may be provided.

After the sampler has completed its sequence, the individual syringes are removed by release of the thumbscrew 210 and removal of the U-shaped guide plate 230. The samplers placed along the downwind direction of the plume are unloaded and the syringes are capped with the cap member 66 described with respect to FIG. 1 and delivered to the analysis section 14.

The analysis section includes at least four GC-EC detectors 250 as described in FIG. 1, each including an inlet assembly 252 adapted to receive the outlet fitting 254 of the syringes 26. The output from each detector is applied to a digital integrator 204.

With four GC-EC lines, by the time the operator has injected sample four into the fourth GC-EC, the first GC-EC has eluted the trailing oxygen band and is ready to accept the fifth sample. The convenient lock-fitting injection system, parallel line GC-EC's and automated integrator recorder permits the operator to run 50–60 samples per hour. The automatic sequential sampler in combination with the multiple-mode GC-EC analyzer allows a few technicians to run a major field study and analyze the samples in a working day or less.

Each GC-EC detector includes a sampling valve 256, having an inlet assembly 252, a carrier gas inlet 258, a calibration gas inlet 260 and a calibrated sample loop 262. A first manifold 264 is connected through molecular sieve filter 261 to regulated carrier gas supply 268. Branch lines containing valves 270, 272, 274, 276 connect the manifold to the individual carrier gas inlets 258.

A second manifold 278 containing valve 80 is connected to the outlet to the calibration cube 282. The cube contains a vaned magnetic stirrer 284 and is mounted on magnetic stirring unit 286. The inlet 288 is connected to a regulated supply of air 290. Branch lines containing valves 292, 294, 296, 298 connect the second manifold 278 to the calibration inlets 260.

The outlet from each GC flows into an EC detector 300, each connected to pulsed voltage source 301. The signal from each detector 300 is amplified in electrometer 305 and digitally integrated in multiple channel integrator 204.

Most chromatographic data is obtained as a series of analog peaks via strip chart recorders and sample composition is calculated from the peak areas. Many manual techniques for peak integration have evolved over the years. These include planimetry, height times width at half height, triangulation, and cutting and weighing of paper. All of these are tedious, time consuming and limited in accuracy and precision. An early development in automatic quantitation was the ball and disc integrator, a low-cost electro-mechanical device which automatically integrates peak areas as they are plotted on recorders. Currently, the disc integrator is perhaps the most widely employed method of integration. It provides a good accuracy and precision at a low cost, but requires considerable operator skill and time.

As the complexity of chromatograms increased due to the higher resolution of new column types and the linear dynamic range of detectors increased up to $10^6$, it became increasingly more difficult to quantitate chromatograms by these manual means. These more demanding requirements led to the development and introduction of the electronic digital integrator, an instrument which provides automatic peak detection, baseline correction, integration and printout of retention times and peak areas.

Digital integrators, however, have two important shortcomings. First, they provide no calculation of final results and secondly, better peak detection, baseline correction and noise filtering is needed for some applications. Further, many digital integrators merely sample a point on the signal at specific time intervals rather than continuously processing the data and integrating the entire area under the curve.

Figure 7:
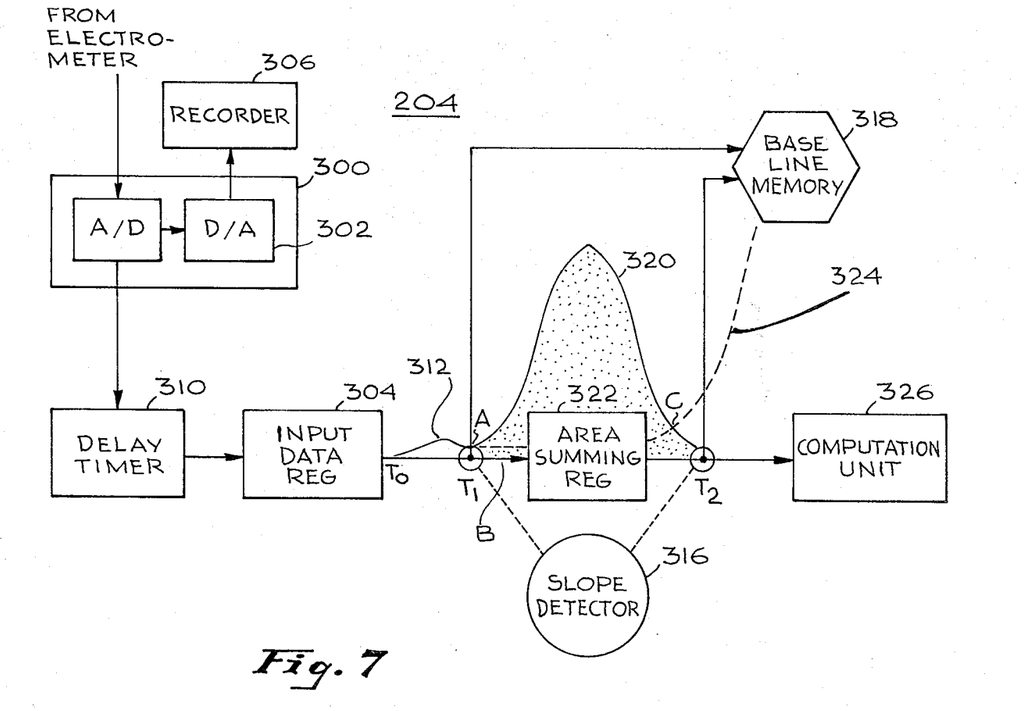
FIG. 7 is a schematic and block diagrammatic view of a computing digital integrator for use with the analytical system of the invention.

Referring now to FIG. 7, each channel module 300 contains a preamplifier and an A/D converter which converts the analog signal from the electrometer 305 to a signal having a frequency proportional to the voltage level. Digital transmission of the signal allows maximum rejection of AC line noise, virtually eliminating noise pick-up and signal degradation which are severe problems in the transmission of low level analog signals.

Also, digital information may be transmitted without deterioration, since digital signals, unlike analog signals, can be regenerated with only a small probability of error. Since the signals are in digital form, they are not subject to phase shifting and other distortions so common with analog signals.

The frequency signal is fed simultaneously to an electrically isolated frequency to voltage converter 302 and to the input data register 304. The isolation of converter 302 prevents electrical feedback from the recorder 306 to the computing integrator 204.

An input data register 304 interfaces each channel module 300 with the data processing unit of the integrator 204. The frequency signal from the module 300 is integrated over a short interval, typically 100 milliseconds, and digitized in the input data register 304. Thus, the system collects all the data rather than non-continuous time slices characteristic of on-line multiplexed data systems. In the diagram, the key components of the computing digital integrator are shown as rectangles for hardware, circles for firmware and hexagons for memory in the data and logic paths.

An integration delay timer 310 delays integration from $T_0$, time of injection, for about 5–6 seconds in order to disable integration during the pressure pulse 312. A first derivative of the average signal is detected and utilized in slope detector 316. When the slope of the analog chromatographic signal is detected as positive, $T_1$, start of integration, point A, baseline position, and point B, real baseline, are stored in baseline memory 318. The total area of peak 320 is summed in register 322.

Return to baseline B is detected by slope detector 316 and the level C of the shifted baseline and time of peak termination, $T_2$, are stored in baseline memory 318. Detection of $T_2$ can be utilized to disable integration during passage of the oxygen band 324 through the detector or integration can be disabled by a timer control. Baseline correction is calculated in the computation unit 326 by subtracting the trapezoidal area bounded by $T_1$, A, C, $T_2$ from the total area summed in register 322. Trapezoidal baseline correction is only possible when the previous baseline level is stored in memory and represents a major performance advantage over conventional digital integration.

The logic and memory functions would be performed by using digital integrators to interface and a mini computer or timeshare terminal for calculations and file storage capability. The hybrid systems offer no fundamental enhancement of operating performance over integrators themselves. On-line computer, data based systems typically have sophisticated programs for peak detection and baseline correction but often suffer a noise problem in transmission and multiplexing of low level analog signals and have high entry and maintenance costs. Therefore, the special purpose chromatographic automated computing integrators such as the System I of Autolab division of Spectra-Physics Corporation are preferred.

It is to be understood that only preferred embodiments of the invention have been described, and that numerous substitutions, alterations and modifications are all permissible without departing from the spirit and scope of the invention as defined in the following claims.

What is claimed is:

1. A gas analysis system comprising in combination:
   a piston-pump sampler comprising a hypodermic syringe including a synthetic, plastic housing defining a sample chamber, a piston housed with the chamber, a plunger secured to the piston and extending out of one end of the chamber, an outlet at the other end of the chamber and a threaded annular member secured to said body surrounding said outlet;
   a gas analysis unit having an inlet adapted to sealingly engage the threaded annular member of the sampler outlet during injection of sample into the unit;
   a needle assembly configured to sealingly and releasably engage said threaded annular member; and
   a sealing member adapted to releasably and sealingly engage said threaded annular member.

2. A system according to claim 1 in which the gas analysis unit is a gas chromatograph with an electron-capture detector.

3. A system according to claim 1 in which the annular member is cylindrical and contains internal threads and concentrically surrounds a short deformable outlet tube connected to the outlet and said inlet member contains an outer shoulder member for engaging said threads and an inner tapered recess for sealingly engaging said tube.

* * * * *